United States Patent
Detweiler (10) Patent No.: US 12,426,900 B2
(45) Date of Patent: Sep. 30, 2025

(54) FASTENER GUIDE

(71) Applicant: Biomet Microfixation, LLC, Jacksonville, FL (US)

(72) Inventor: Jason F. Detweiler, Warsaw, IN (US)

(73) Assignee: Biomet Microfixation, LLC, Jacksonville, FL (US)

( * ) Notice: Subject to any disclaimer, the term of this patent is extended or adjusted under 35 U.S.C. 154(b) by 303 days.

(21) Appl. No.: 18/108,908

(22) Filed: Feb. 13, 2023

(65) Prior Publication Data

US 2023/0255649 A1     Aug. 17, 2023

Related U.S. Application Data

(60) Provisional application No. 63/310,718, filed on Feb. 16, 2022.

(51) Int. Cl.
*A61B 17/17*       (2006.01)
*A61B 17/80*       (2006.01)

(52) U.S. Cl.
CPC .............. *A61B 17/17* (2013.01); *A61B 17/80* (2013.01)

(58) Field of Classification Search
CPC ..... A61B 17/17; A61B 17/80; A61B 17/1728; A61B 17/808; A61B 17/8875; A61B 17/8894
See application file for complete search history.

(56) References Cited

U.S. PATENT DOCUMENTS

| | | | | |
|---|---|---|---|---|
| 5,314,431 | A * | 5/1994 | Graziano | A61B 17/8863 606/103 |
| 9,820,793 | B1 * | 11/2017 | Wade | A61B 17/8869 |
| 10,159,503 | B2 * | 12/2018 | Niederberger | A61B 17/1728 |
| 2020/0337751 | A1 * | 10/2020 | Detweiler | A61B 17/8038 |
| 2021/0177472 | A1 | 6/2021 | Detweiler et al. | |

\* cited by examiner

*Primary Examiner* — Tracy L Kamikawa
(74) *Attorney, Agent, or Firm* — SCHWEGMAN LUNDBERG & WOESSNER, P.A.

(57) ABSTRACT

A disclosed fastener guide includes first and second longitudinal body portions that include, respectively, first and second distal segments. These body portions are connected together to form a fastener through-bore therebetween into which a fastener can be received for guiding the fastener into a hole in a bone plate. This connection can be flexible to allow the fastener guide to move between open and closed positions. In the closed position, a spacing of the first and second distal segments relative to one another is such that a combination of the two can be received in the hole in the bone plate for attaching the fastener guide to the plate; however, in the open position, this combination can no longer be received in the hole due to the segments being spaced relatively further apart from one another in comparison to the spacing in the closed position of the fastener guide.

15 Claims, 10 Drawing Sheets

FASTENER GUIDE

CLAIM OF PRIORITY

This application claims the benefit of U.S. Provisional Patent Application Ser. No. 63/310,718, filed on Feb. 16, 2022, the benefit of priority of which is claimed hereby, and which is incorporated by reference herein in its entirety.

BACKGROUND OF THE INVENTION

1. Field of the Invention

The present invention relates generally to bone closure devices for securing bone portions together, and more particularly, to a driven screw guide for use with a bone plate.

2. Description of the Related Art

Some surgical procedures involve separating a bone into portions and reuniting the bone portions after conducting the desired operation within the body. Various devices are used to refix or resecure the bone portions to one another. For example, in a sternal reapproximation medical procedure, one or more sternal fixation or closure devices can be used to hold and secure the portions of the sternum together. Generally, each sternal fixation device will engage or otherwise wrap around the sternal portions in order to hold and secure the sternal portions together. One such fixation device is a bone plate with one or more threaded holes for receiving bone screws therein. The bone plate spans across the bone portions, and upon screwing the bone screws into the bone portions, the bone plate holds the bone portions together.

A positioning device or screw guide may be used in conjunction with a bone plate to help guide the bone screw into the bone plate. A screw guide may include a screw cartridge with multiple screws therein. Further, the screw guide typically has a tubular body with a channel or through-bore, which receives the bone screw and guides the screw to the desired threaded hole in the bone plate and on into the bone. The screw guide may also guide the screwdriver or drill bit which screws the bone screw into the threaded hole of the bone plate.

What is needed in the art is an easy-to-use screw guide for easily retaining and guiding a screw into a bone plate.

SUMMARY OF THE INVENTION

The present invention provides, in some embodiments, a fastener guide that comprises a first longitudinal body portion including a first distal segment and a second longitudinal body portion including a second distal segment. The first longitudinal body portion can be connected to, linked or otherwise associated with the second longitudinal body portion, for example, to form a fastener through-bore therebetween into which a fastener can be received for guiding the fastener into a hole in a bone plate. The first longitudinal body portion being so connected to the second longitudinal body portion can comprise a flexible connection, a bendable connection, a hinged connection, a pivot connection, or the like between the first longitudinal body portion and the second longitudinal body portion to allow the fastener guide to move between an open position and a closed position. In such a closed position, for example, a spacing of the first distal segment and the second distal segment relative to one another can be such that a combination of the first distal segment and the second distal segment can be received in the hole in the bone plate for attaching the fastener guide to the bone plate; however, in the open position of the fastener guide in this example, this combination can no longer be received in the hole in the bone plate due to the first distal segment and the second distal segment being spaced relatively further apart from one another in comparison to the spacing in the closed position of the fastener guide. Such a fastener guide can further include a first retaining member, for example, incorporated into the first longitudinal body portion for retaining the fastener in the fastener through-bore. In some aspects, at least part of this first retaining member will be positioned proximally of the pivot or other connection or association between the body portions along the fastener guide. Additionally, such a fastener guide can include a first biasing element, for example, incorporated into the first longitudinal body portion for biasing the fastener guide toward the open position when in the closed position. In some aspects, at least part of this first biasing element can be positioned distally of the pivot or other connection or association between the body portions along the fastener guide. Such a fastener guide can be combined with a fastener and/or a bone plate, for example, as discussed elsewhere herein. For example, a fastener can be received and retained in the fastener through-bore with the fastener guide attached to the bone plate in the closed position. Additionally, such a fastener guide can be made such that each of the first distal segment and the second distal segment incorporates a threaded section or otherwise shaped section. Such a section can be specifically shaped for mating with a threaded or otherwise-shaped portion of a hole in a bone plate. Additionally, such a fastener guide can be made to include a second biasing element, for example, incorporated into the second longitudinal body portion for biasing the fastener guide toward the open position when in the closed position. In some aspects, at least part of this second biasing element can be positioned distally of the pivot or other connection or association between the body portions along the fastener guide. Additionally, such a fastener guide can be made such that, in the closed position of the fastener guide, the first biasing element and the second biasing element can be in opposing contact with one another. Optionally thereafter, these elements can exert force against one another to move the fastener guide from the closed position to the open position. Additionally, such a fastener guide can be made such that the first longitudinal body portion incorporates a pair of biasing elements which includes the first biasing element, and the second longitudinal body portion incorporates a pair of biasing elements which includes the second biasing element.

Additionally, the present invention provides, in some embodiments, a fastener guide that comprises a first longitudinal body portion including a first distal segment (e.g., threaded) and a second longitudinal body portion including a second distal segment (e.g., threaded). Such a first longitudinal body portion can be connected to, linked or otherwise associated with the second longitudinal body portion to form a fastener through-bore therebetween, for example, one into which a fastener can be received for guiding the fastener into a hole in a bone plate. For example, such an association between a first longitudinal body portion and a second longitudinal body portion can comprise a flexible connection, a bendable connection, a hinged connection, a pivot connection, or the like between the first longitudinal body portion and the second longitudinal body portion, for example, to allow the fastener guide to move between an open position and a closed position. In some forms, when the fastener guide is in the closed position, a spacing of the first distal segment and the second distal segment relative to one another can be such that a combination of the two can be received (e.g., threadably received) in a hole in a bone plate for attaching the fastener guide to the bone plate; however, when the fastener guide is in the open position, this combination can no longer be received in the hole in the bone plate due to the first distal segment and the second distal segment being spaced relatively further apart from one another in comparison to the spacing in the closed position of the fastener guide. Optionally, such a fastener guide can include a first retaining member incorporated into the fastener guide (e.g., into the first longitudinal body portion) for retaining the fastener in the fastener through-bore. Optionally, such a fastener guide can include a first biasing element incorporated into the fastener guide (e.g., into the first longitudinal body portion) for biasing the fastener guide toward the open position when in the closed position. Optionally, such a fastener guide can be made such that at least part of the first retaining member can be positioned proximally of the pivot or other connection or association between the body portions along the fastener guide. Sometimes the entirety of the first retaining member will be so positioned. Optionally, such a fastener guide can be made such that all or part of the first biasing element is positioned distally of the pivot or other connection or association between the body portions along the fastener guide. Optionally, such a fastener guide can be made to further comprise a second biasing element incorporated into it (e.g., into the second longitudinal body portion) for biasing the fastener guide toward the open position when in the closed position. In such forms, when in the closed position of the fastener guide, the first biasing element and the second biasing element can be in opposing contact with one another, for example, such that thereafter the two elements can exert force against one another to move the fastener guide from the closed position to the open position.

Addition, the present invention provides, in some embodiments, a driven fastener guide for guiding a fastener into a hole of a bone plate. Such a driven fastener guide can comprise an elongated driver configured for connecting to a drill and a fastener guide member operably connected to the elongated driver. The fastener guide member can include a first section and a second section which is pivotably connected or otherwise connected or associated with the first section. The first section and the second section can define a through-bore configured for receiving the fastener. The fastener guide member can be configured for aligning the fastener relative to the hole of the bone plate. The first section can include a first distal end, and the second section can include a second distal end. The first distal end and the second distal end can be biased to an open position relative to one another. Optionally, the first section includes at least one first biasing element and the second section includes at least one second biasing element, for example, where the at least one first biasing element and the at least one second biasing element oppose one another so as to bias the first distal end and the second distal end to the open position. In addition, the driven fastener guide can be made so as to include a belt which connects (e.g., pivotably connects) the first section and the second section together.

BRIEF DESCRIPTION OF THE DRAWINGS

The above-mentioned and other features and advantages of the inventions disclosed herein, and the manner of attaining them, will become more apparent, and the inventions will be better understood by reference to the following descriptions of embodiments of the inventions taking in conjunction with the accompanying drawings, wherein.

Corresponding reference characters indicate corresponding parts throughout the several views. The exemplifications set out herein illustrate embodiments of the invention and such exemplifications are not to be construed as limiting the scope of the invention in any manner.

DETAILED DESCRIPTION OF THE INVENTION

The present invention provides in certain embodiments a fastener guide member with two opposing sections pivotably connected to one another, with the distal ends of the sections being biased to an open position.

The disclosure of U.S. patent application publication no. 2021/0177472, entitled "DRIVEN UNIVERSAL SCREW GUIDE", published Jun. 17, 2021 ("the '472 publication," stemming from U.S. patent application Ser. No. 17/117,604, filed Dec. 10, 2020), is incorporated herein by reference in its entirety.

Figure 1:
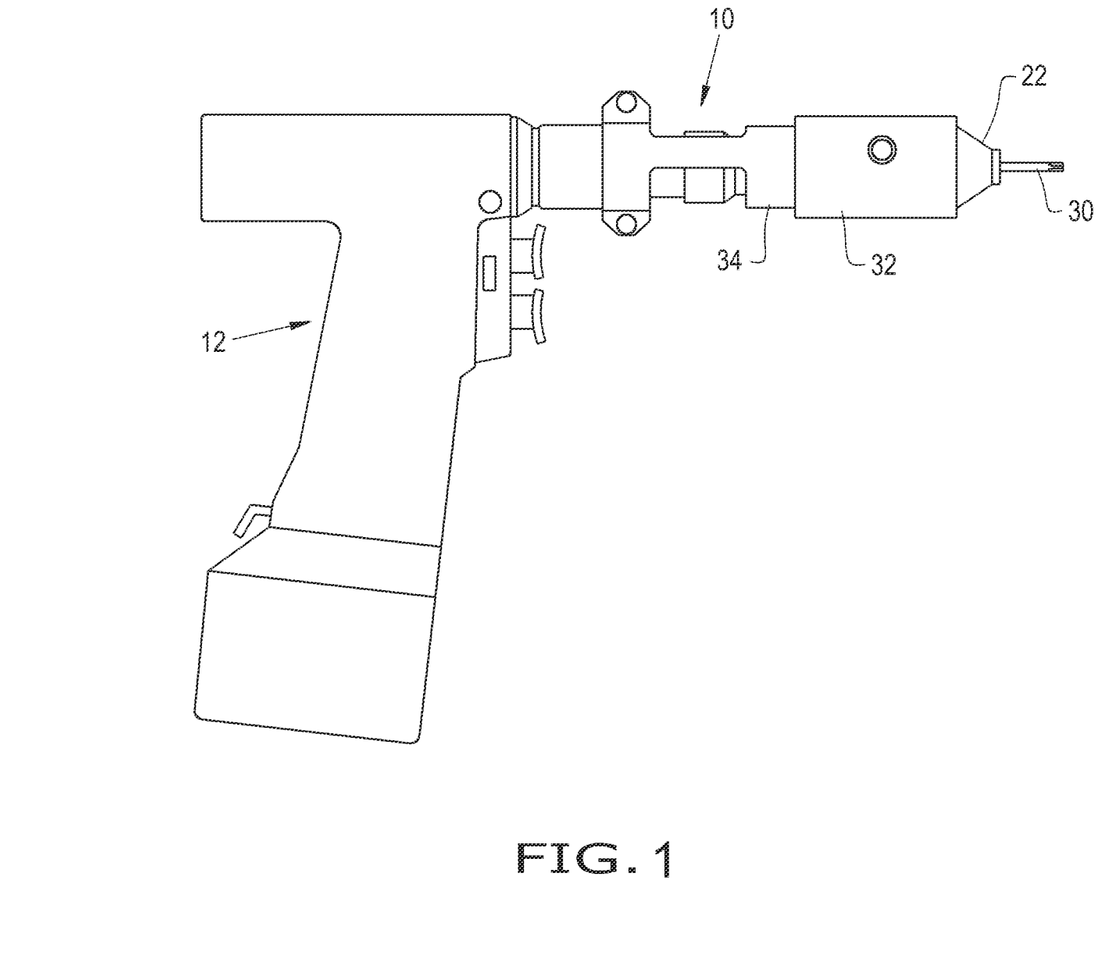
FIG. 1 is a side view of an embodiment of a drill usable with the driven fastener guides disclosed herein.
Figure 9:
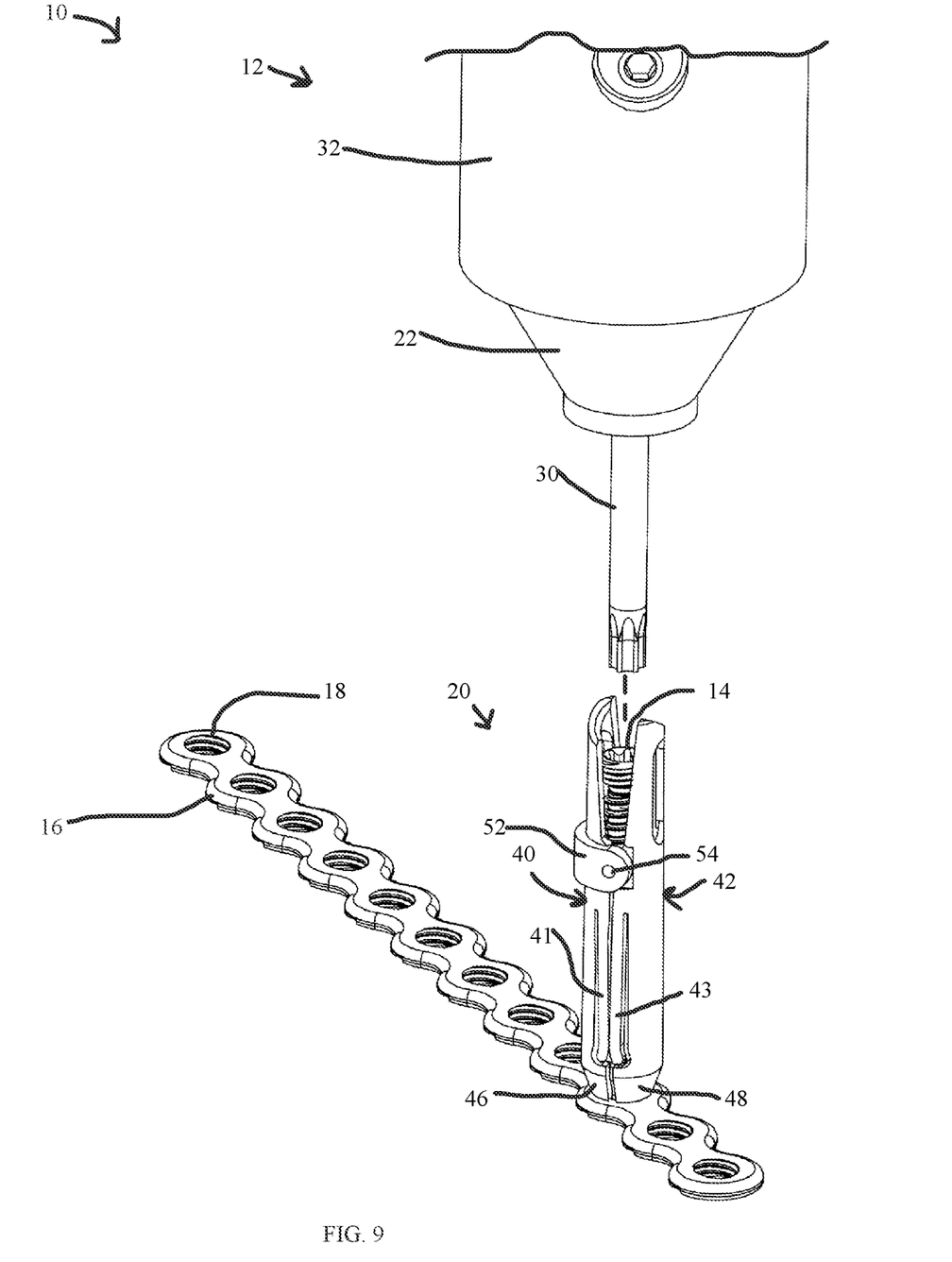
FIG. 9 is a perspective view of the end of the driven fastener guide of FIG. 2, wherein the distal section of the fastener guide is shown to be attached to the bone plate and the screw is positioned within the fastener guide.
Figure 10:
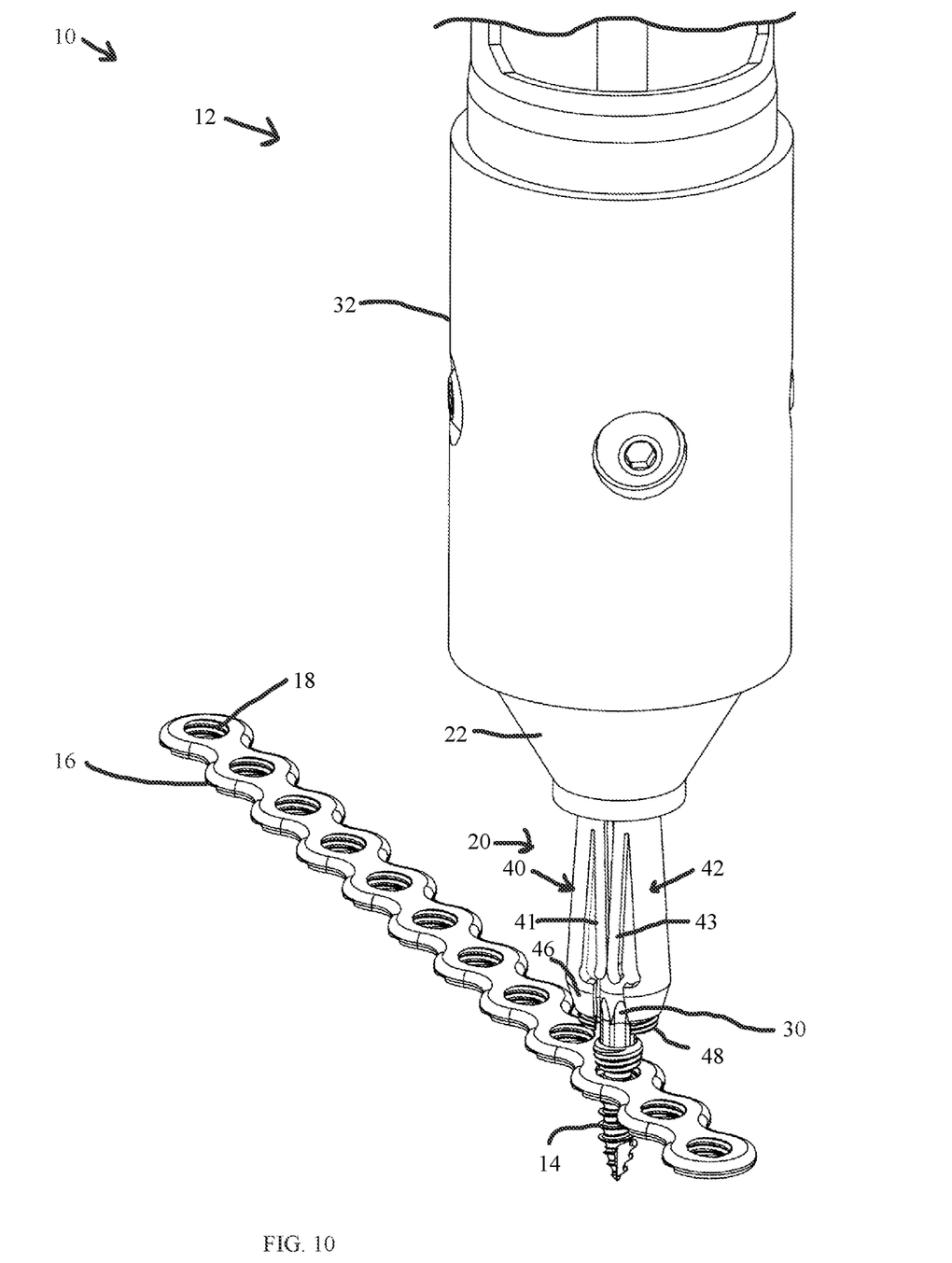
FIG. 10 is a perspective view of the end of the driven fastener guide of FIG. 2, wherein the distal section of the fastener guide is shown to be detached from the bone plate and the screw is at least partly received in the bone plate.

Referring now to the drawings, and more particularly to FIG. 1, there is shown a side view of a drill which can be used in conjunction with a driven fastener guide of the present invention in order to insert a fastener, such as a bone screw, into a bone, in order to secure a fixation device, such as a bone plate, to the bone. The drill can be a hand-held drill, such as electric drill 12 (also shown in FIG. 7 of the '472 publication). Drill 12 is shown attached to driven fastener guide 10, which is capable of collectively holding, guiding, and inserting fasteners 14 (i.e., a bone screw, a marking device, a peg, a headless pin, etc.) into variously configured fixation devices, such as a bone plate 16 (screw 14 and plate 16 are shown in FIGS. 9-10). Driven fastener guide 10 is also capable of removing and holding fasteners 14 therein. In operation, driven fastener guide 10 may removably engage with bone plate 16 for easily guiding fastener 14 into or out of bone plate 16.

Alternatively to being driven by an electric drill 12, the driven fastener guide 10 may be manually driven. For instance, the driven fastener guide 10 may connect to a handle portion for allowing a user to manually rotate the driven fastener guide 10. The driven fastener guide 10 may include any desired material, such as metal and/or plastic. Thereby, the drill 12 may be in the form of any desired electric and/or manually operated drill 12. FIG. 1 further shows that driven fastener guide 10 includes drill mount 34, housing 32, collar 22 (which can also be referred to as a stem mounting member), and elongate driver 30.

Figure 4:
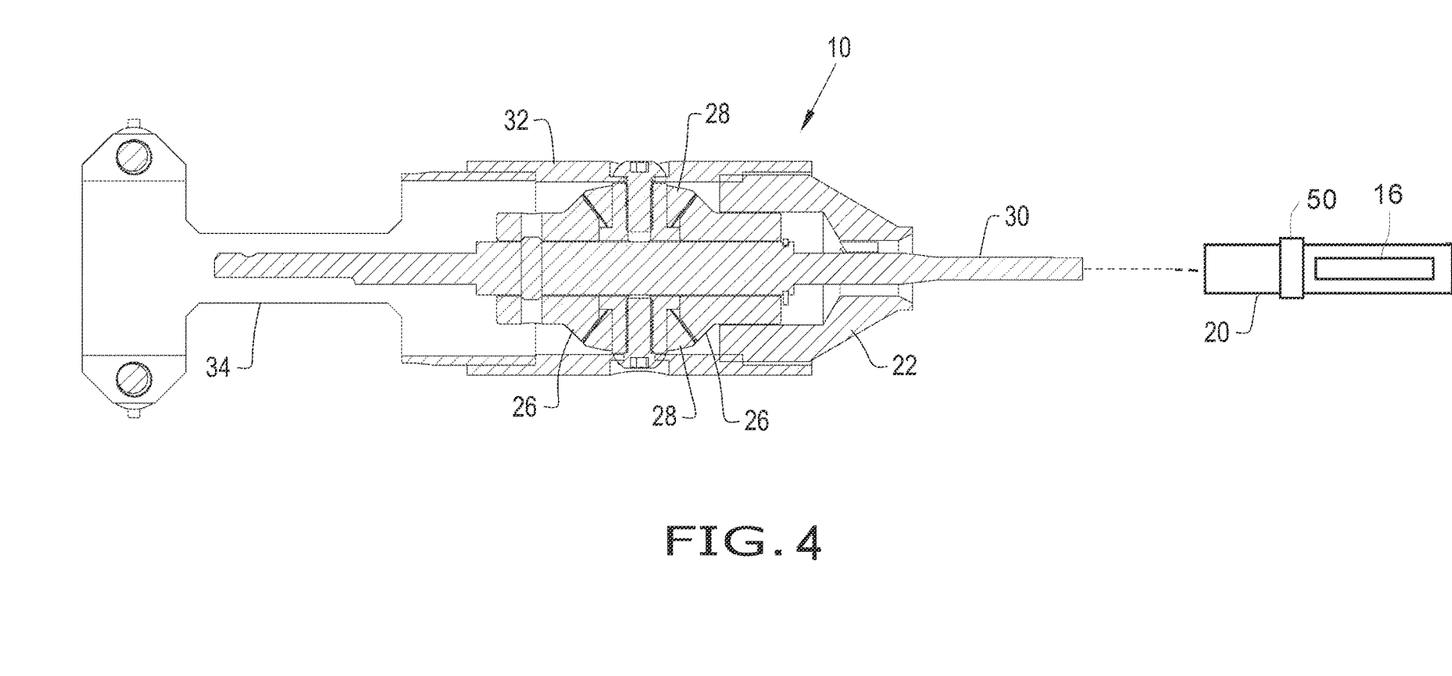
FIG. 4 is a cross-sectional view of the driven fastener guide with the guide member being disconnected from the collar.

Drill mount 34 is removably connected to drill 12 by way of a clamping mechanism. Drill mount 34 is connected to housing 32 and thus removably connects housing 32 to drill 12 by way of the clamping mechanism. Drill mount 34 provides a stable and sturdy connection between housing 32 and drill 12. It should be appreciated that driven fastener guide 10 may not include drill mount 34 such that only elongated driver 30 is operably coupled to drill 12. In such a configuration, the user may manually hold onto housing 32 to make collar 22 spin in reverse (the reverse action of collar 22 relative to elongated driver 30 is explained below). Also, driven fastener guide 10 may be fixedly attached to drill 12. Housing 32 may be connected to drill mount 34. Housing 32 may extend over at least a portion of drill mount 34 and collar 22, respectively (FIG. 4). Housing 32 may have a substantially tubular body with a circular cross-section. Housing 32 may also have internal grooves and/or protrusions for securing or otherwise accommodating drill mount 34, gears 26, 28 (explained below), and/or collar 22. Collar 22 is discussed more fully below. Elongated driver 30 has one end for connecting to drill 12 and an opposite end for connecting to screw 14. Elongated driver 30 may also movably engage with collar 22 via one or more bearings. Elongated driver 30 may be in the form of a drill bit 30. It should be appreciated that a distal end of elongated driver 30 may have any desired configuration for engaging with any desired screw 14.

Figure 2:
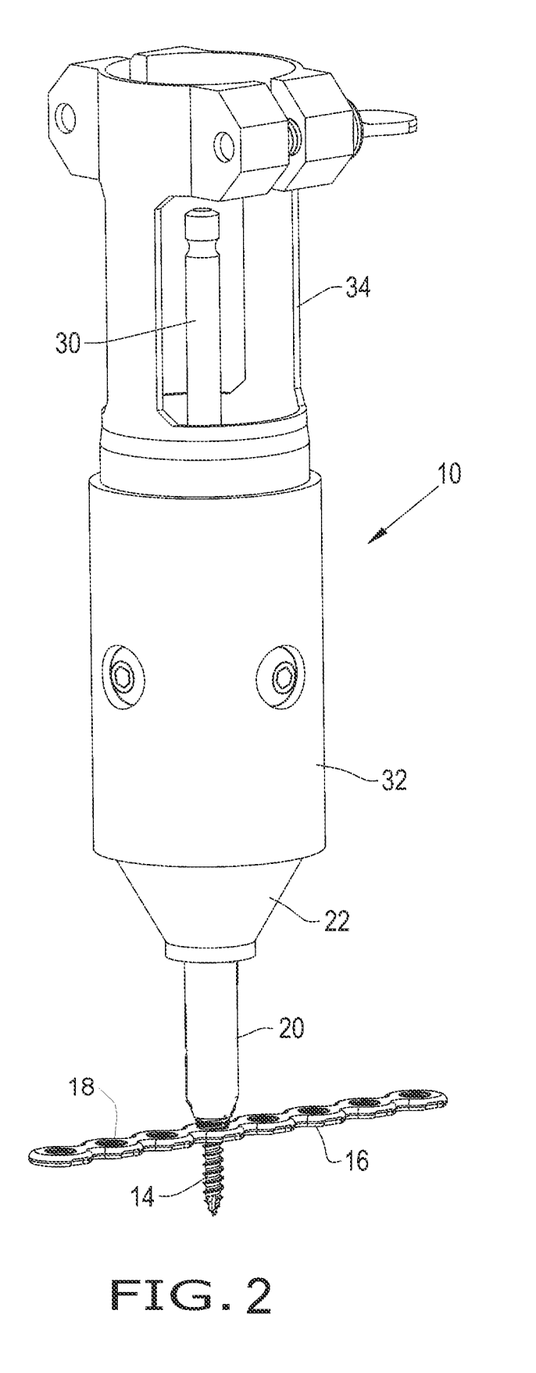
FIG. 2 is a perspective view of an embodiment of a driven fastener guide for driving a screw into a bone plate where the driven fastener guide includes a guide member, a collar, a gearing assembly, an elongated driver bit, and a housing.

Referring now to FIG. 2, there is shown a perspective view of driven fastener guide 10, which further includes a stem or fastener guide member 20 (which can be referred to as fastener guide 20 herein). Fastener guide 20 can be elastically deformable, at least in part. Fastener guide member 20 is shown schematically in FIGS. 2-4. In FIG. 2, fastener guide member 20 is shown mounted to collar 22 and to include a belt 52 (which can also be referred to as a collar 52), with screw 14 extending from fastener guide member 20 and through a respective hole 18 in bone plate 16. When fastener 14 is a bone screw, fastener guide 20 can be referred to as a screw guide 20.

Figure 3:
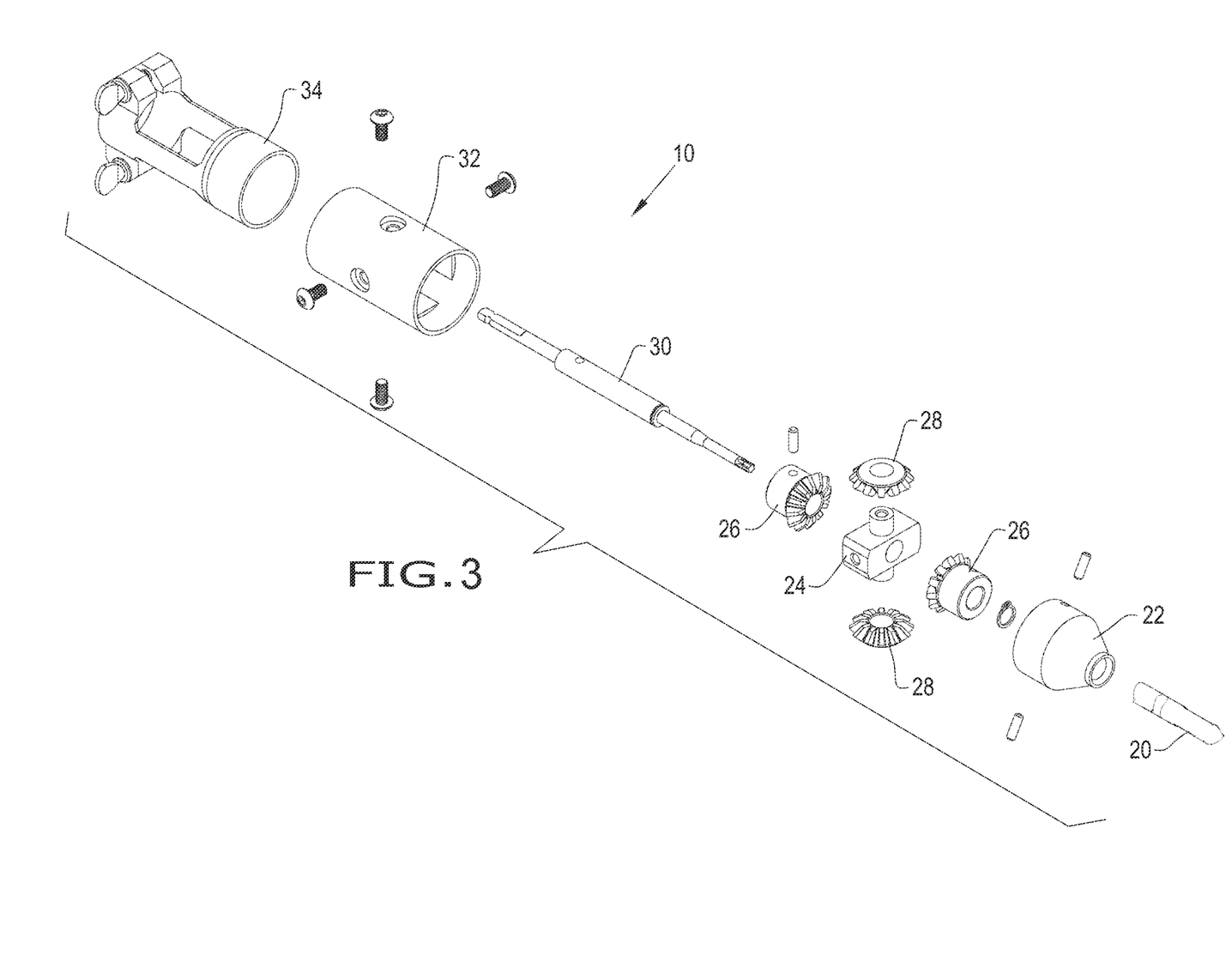
FIG. 3 is an exploded view of the driven fastener guide of FIG. 2.
Figure 5:
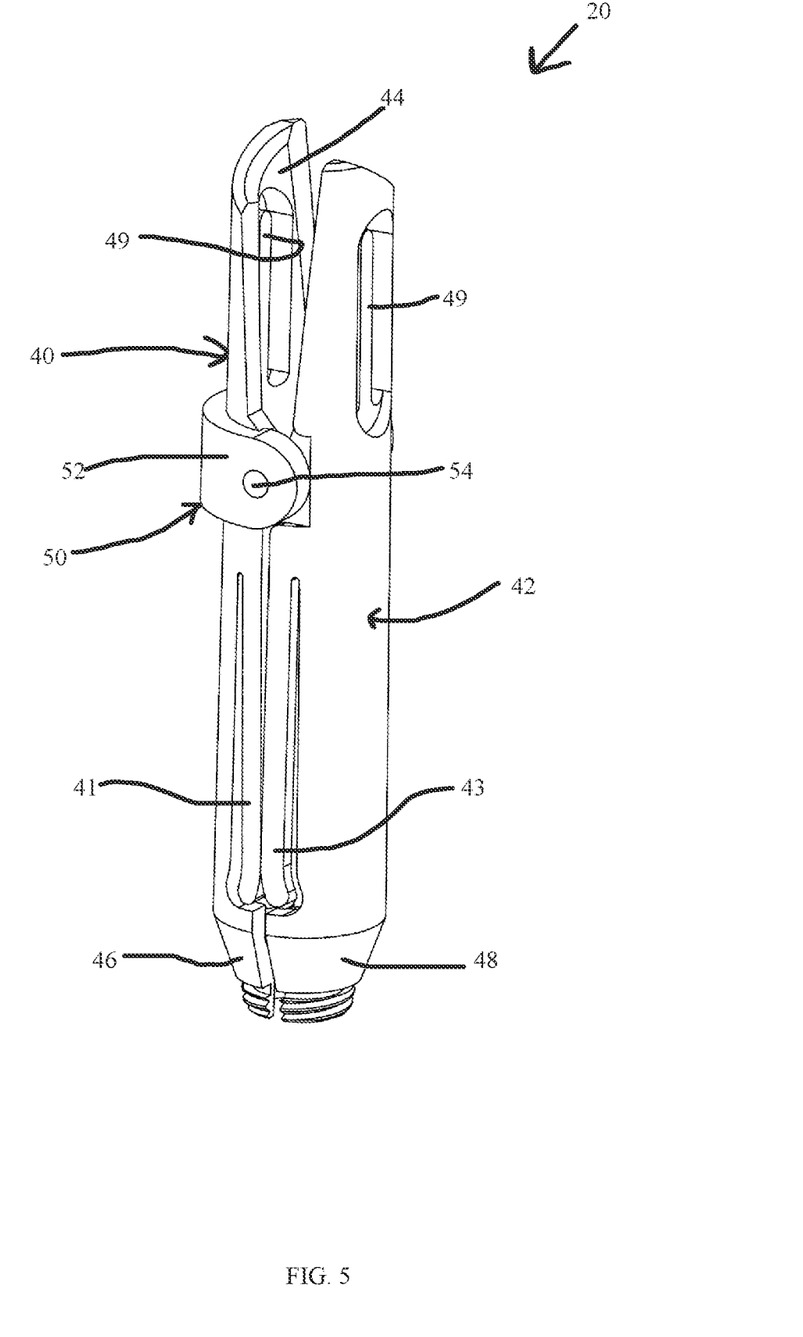
FIG. 5 is a perspective view of an embodiment of a fastener guide disclosed herein in a closed position.

Referring now to FIGS. 3 and 4, there is shown an exploded view of driven fastener guide 10 (FIG. 3) and a cross-sectional view of driven fastener guide 10 (FIG. 4). The driven fastener guide 10 further includes a gearing assembly including a gear mount 24 which mounts multiple gears 26, 28 thereon. Gears 26, 28 and elongated driver 30 are operably connected together, and elongated diver 30 may also contact and/or mount the gear mount 24 and the gears 26, 28. After inserting fastener 14 into the fastener guide member 20, driven fastener guide 10 may initially align fastener 14 by engaging, e.g. screwing, the end of the fastener guide member 20 with bone plate 16 (FIGS. 5 and 9 show that the distal end of fastener guide member includes threads, which threadably mate with threads of a corresponding hole 18 of bone plate 16). Thereafter, driven fastener guide 10 may simultaneously disengage fastener guide member 20 and insert fastener 14 within bone plate 16. For instance, elongated driver 30 and collar 22 may simultaneously rotate in opposite directions in order to unscrew fastener guide member 20 from hole 18 which allows bone screw 14 to pass through fastener guide member 20 and be accordingly screwed into a respective hole 18. Driven fastener guide 10 may be considered a universal driver 10 since it does not require bone plate 16 to have any additional or separate mating features other than the existing threaded through hole 18 itself.

Fastener guide member 20 is operably connected to elongated driver 30 by way of collar 22. Fastener guide member 20 may be removably attached to collar 22. For instance, fastener guide member 20 can be press-fit within collar 22, coupled to collar 22 by one or more fasteners, have one or more mating features which selectively engage with corresponding mating features of collar 22, and/or simply be received within collar 22 without being permanently fixed to collar 22. Additionally, for example, protrusions inside collar 22 may engage with corresponding removal slots (such as elongate slots at a proximal end of each section 41, 42 in which beam 49 projects) of fastener guide member 20. Collar 22 may be connected to housing 32 and a gear 26 via one or more fasteners, such as pins, screws, bolts, etc. Collar 22 may also removably mount fastener guide member 20. For instance, collar 22 and fastener guide member 20 may each include a corresponding mating feature, e.g. corresponding groove(s) and protrusion(s). Additionally, collar 22 could also be fitted with a retaining feature, e.g. magnet, ball detent, etc., to retain fastener guide member 20 and prevent unattended disassociation between collar 22 and fastener guide member 20. Collar 22 may also at least partially house any one of gears 26, 28. Collar 22 may include any desired material such as metal and/or plastic.

The gearing assembly of driven fastener guide 10 may generally include gear mount 24, a pair of sun gears 26 in the form of input and output gears 26 mounted on elongated driver 30, and a pair of intermediary, i.e., planetary gears 28 rotatably mounted onto gear mount 24. Gear mount 24 has a center through hole for receiving elongated driver 30 and a pair of protrusions which mount planetary gears 28. The proximal, input gear 26 may be fixedly attached to elongated driver 30 via one or more fasteners. The distal, output gear 26 may be coupled to collar 22 via one or more fasteners. The rotary motion which is inputted by the elongated driver 30 is operably reversed by gears 26, 28 so that collar 22, and fastener guide member 20 therewith, rotate in an opposite direction to elongated driver 30. Driven fastener guide 10 may include any number of gears. The gear ratio may be such that fastener guide member 20 spins faster or slower than elongated driver 30. Alternatively, driven fastener guide 10 may include dual motors for generating the opposition rotation of fastener guide member 20 and elongated driver 30.

Fastener guide member 20 holds and guides screw 14. Fastener guide member 20 also aligns screw 14 by threading into, or otherwise engaging, hole 18 of bone plate 16. Fastener guide member 20 may include any suitable material, such as a metal, a polymer, and/or a plastic.

Referring now to FIG. 5, there is shown a perspective view of fastener guide member 20, with fastener guide member 20 being in the closed position. Fastener guide member 20 includes an upper end and a lower end (the upper end being the top end and the lower end being the bottom end, as shown in the view of FIG. 1). The upper end is a proximal end, and the lower end is the distal end and is the end which connects to bone plate 16. Fastener guide member 20 includes a first section 40, a second section 42 which is pivotably connected to first section 40, and a belt assembly 50. Each of first and second sections 40, 42 form longitudinally extending halves, respectively, of fastener guide member 20. First section 40 and second section 42 together define a through-bore 44 configured for receiving fastener 14 (as shown in FIGS. 9-10). It should be appreciated that fastener guide member 20, by way of through-bore 44, may guide screw 14 and/or any desired tool or device. For instance, fastener guide member 20 may be used to guide bone preparation tools, e.g. drills or taps, prior to insertion of screw 14 into fastener guide member 20. First section 40 includes a first distal end 46, and second section 42 includes a second distal end 48. First and second distal ends 46, 48 can be threaded so as to threadably connect with threads of hole 18 of bone plate 16, though it can be appreciated that distal ends 46, 48 may not be threaded.

Each of first and second sections 40, 42 can include a beam 49, i.e., a retaining member, projecting upwardly from a bottom of a respective slot of each of first and second sections 40, 42. Each beam 49 may extend upwardly and radially inwardly such that each beam 49 at least partially extends into through-bore 44 to cause interference with, i.e., contact, screw 14. Thereby, each beam 49 may help hold screw 14 within through-bore 44 by way of contacting and applying a retention force onto a side of screw 14. Applying a downward force on screw 14, by elongated driver 30, will force beam(s) 49 outwardly so that screw 14 may pass through through-bore 44 of fastener guide member 20. As can be appreciated, each beam 49 may be machined from a respective section 40, 42 of fastener guide member 20 such that a bottom of beam 49 remains coupled with a respective section 40, 42, and a top of beam 49 is free to extend inwardly into through-bore 44. Each beam 49 may extend at least partially, for example substantially, along the length of fastener guide member 20. It should be appreciated that fastener guide member 20 may not include beam 49.

Belt assembly 50 includes a belt 52 and two pivot pins 54. Belt 52 has an arcuate shape and is positioned adjacent first section 40. Belt 52 pivotably connects first and second sections 40, 42 together. Only one pivot pin 54 is shown in FIG. 5, but it can be appreciated that a corresponding pivot pin 54 is on the other side of fastener guide member 20. Pivot pins 54 secure belt 52 to first and second sections 40, 42 such that belt 52 and pivot pins 54 pivotably connect first and second sections 40, 42 about a transverse axis extending through pivot pins 54. Pivot pins 54, together with belt 52, thus forms a hinge about which first and second sections 40, 42 can pivot relative to one another between a closed position (FIGS. 5 and 9) and an open position (FIGS. 6, 7, 10), the closed position being when first and second distal ends 46, 48 are relatively close to one another, the open position being when first and second distal ends 46, 48 are relatively farther away from one another.

Each of first and second distal ends 46, 48 are biased to the open position relative to one another. This biasing can be accomplished by way of at least one biasing element. More specifically, according to an exemplary embodiment of the present invention, first section 40 includes at least one biasing element 41, and second section 42 includes at least one biasing element 43, biasing elements 41, 43 being substantially similar to one another. The at least one biasing element 41 and the at least one biasing element 43 oppose one another so as to bias first distal end 46 and second distal end 48 to the open position. According to an exemplary embodiment of the present invention, the at least one biasing element 41 can be formed as a pair of leaf springs 41, and the at least one biasing element 43 can be formed as a pair of leaf springs 43. Each leaf spring 41, 43 can be machined into a respective one of the first and second sections 40, 42.

Though only one leaf spring 41, 43 is shown in each of first and second sections 40, 42 in FIG. 5, it can be appreciated that a corresponding leaf spring 41, 43 is on the other side of first and second sections 40, 42. During manufacture of fastener guide member 20, after leaf springs 41, 43 are machined into first and second sections 40, 42, each leaf spring 41, 43 can be bent outwardly (toward the opposing section 40, 42) in order to provide the spring effect to the open position.

Figure 6:
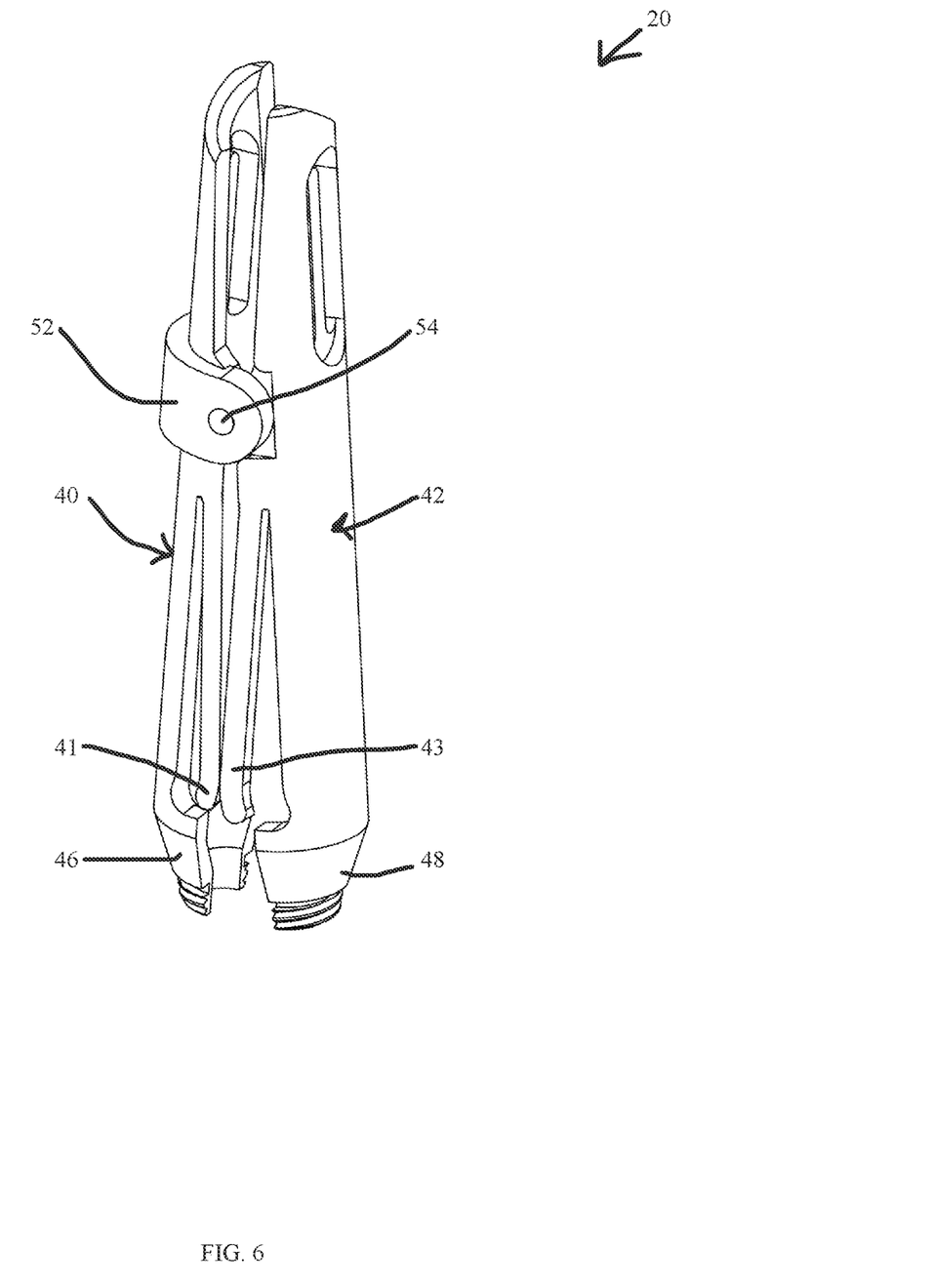
FIG. 6 is a perspective view of the fastener guide of FIG. 5 in an open position.

Referring now to FIG. 6, there is shown a perspective view of fastener guide member 20. The difference between FIGS. 5 and 6 is that in FIG. 6 fastener guide member 20 is in the open position. Here, distal ends 46, 48 are farther away from each other than in FIG. 5. This open position is the normal position, given the biasing of leaf springs 41, 43. Thus, to move fastener guide member 20 to the closed position, pressure needs to be exerted radially inwardly on distal ends 46, 48 (or at least distal of the hinge provided by belt assembly 50). Releasing this pressure enables distal ends 46, 48 to move apart from one another, by the biasing force of leaf springs 41, 43 exerted against one another. For, leaf springs 41, 43 mirror one another and are in contact with one another, as shown in FIG. 6.

Figure 7:
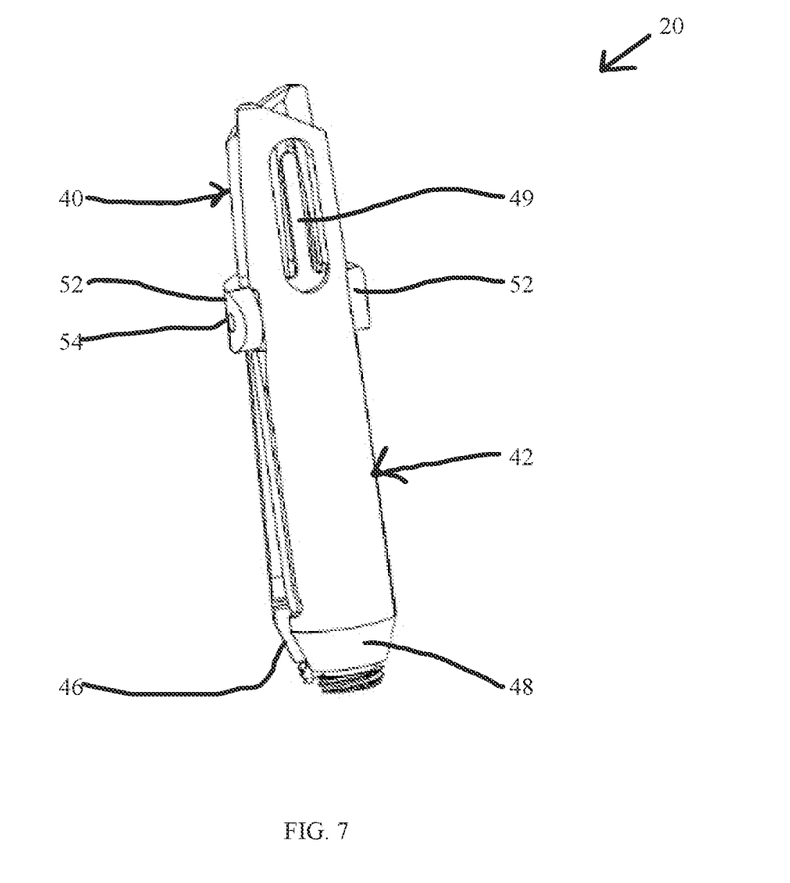
FIG. 7 is an alternative perspective view of the fastener guide of FIG. 5 in an open position.

Referring now to FIG. 7, there is shown a perspective view of fastener guide member 20, but viewing primarily second section 42. Fastener guide member 20 is in the open position. More visible in FIG. 7 is the slot and a corresponding beam 49.

Figure 8:
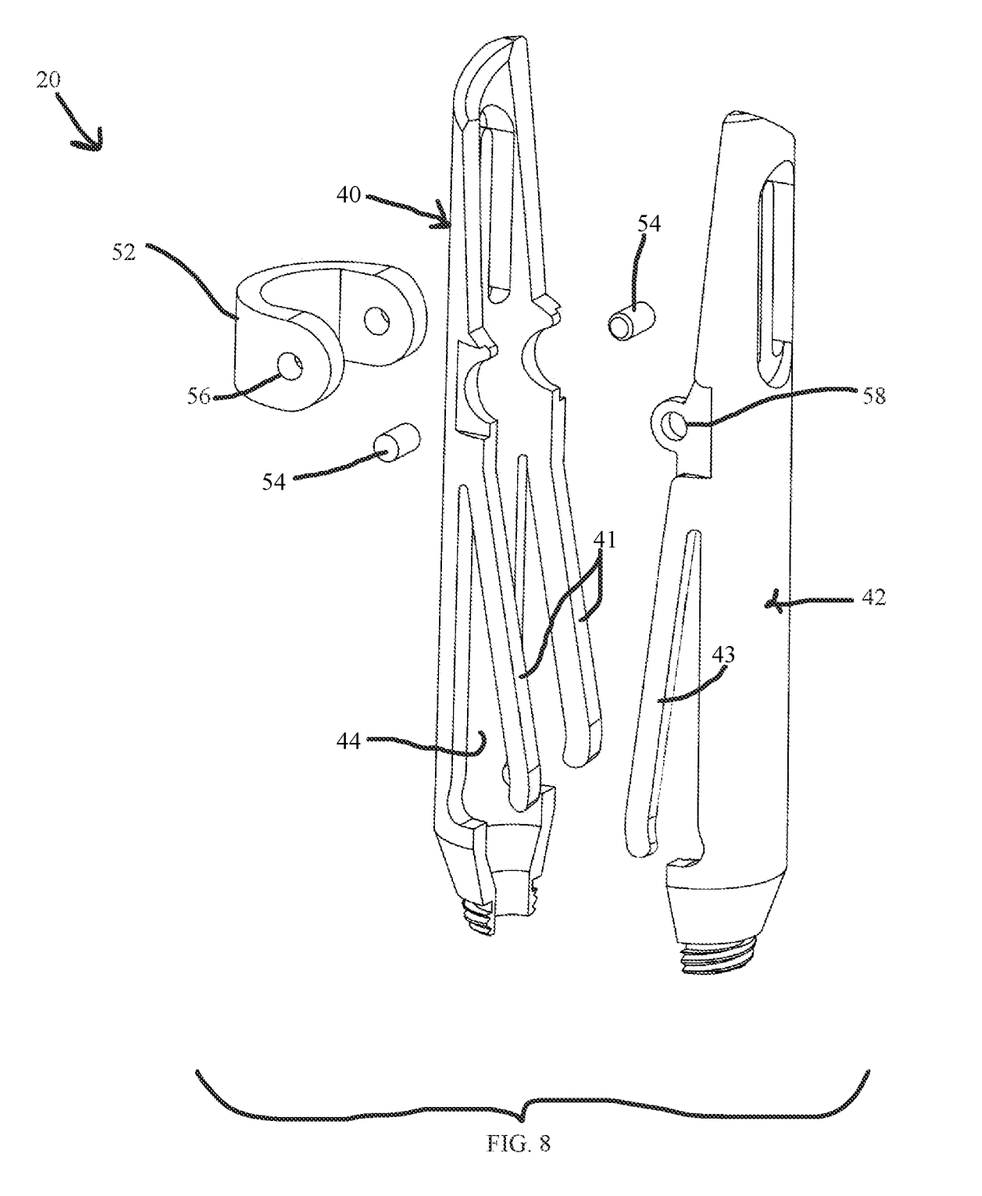
FIG. 8 is an exploded, perspective view of the fastener guide of FIG. 5.

Referring now to FIG. 8, there is shown an exploded, perspective view of fastener guide member 20. Belt 52 includes opposing holes 56. Second section 42 includes opposing holes 58 formed in a convex boss, which is matingly received in a concave portion of section 40. Upon locating these convex bosses in the concave portions, belt 52 can be seated around section 40 such that holes 56 align with holes 58, and then pins 54 can be positioned in holes 56, 58. Pins 54 can be secured to 56, 58 in any suitable manner, including welding, friction fit, or the like, but leaving the ability for first section 40 and/or second section 42 to pivot about the transverse axis through pins 54. Leaf springs 41, 43 are shown extending towards one another.

Referring now to FIG. 9, there is shown driven fastener guide 10. Drill 12 is shown to include housing 32 and collar 22. Fastener guide 20 is spaced apart from collar 22, and elongated driver 30 has not yet engaged fastener 14, which is positioned in through-bore 44 of fastener guide 20. Fastener guide 20 is in the closed position, and distal ends 46, 48 are engaged, such as threadably engaged, with threads of a respective hole 18 of bone plate 16. Fastener guide 20 is in the closed position. In use, elongated driver 30 will descend to engage a head of fastener 14.

Referring now to FIG. 10, there is shown driven fastener guide 10. Drill 12 is shown to include housing 32 and collar 22, which has received a proximal end of fastener guide 20, including belt assembly 50. Collar 22 can engage with a portion of fastener guide 20 proximate to belt assembly 50 and/or engage with belt 52. Fastener guide 20 is in the open position, with distal ends 46, 48 being disengaged and spaced apart from bone plate 16. Being disengaged from bone plate 16, sections 40, 42 have spread apart form each other at their distal ends 46, 48 by way of leaf springs 41, 43. In this way, FIG. 10 shows fastener guide 20 in the open position.

In use, sections 40, 42 of fastener guide 20 can be squeezed together, such that distal ends 46, 48 are in the closed position. This enables distal ends 46, 48 to threadably engage the threads of hole 18 and also enables fastener 14 to be retained in through-bore 44 between sections 40, 42. This squeezing can occur manually by the user, and/or can be accomplished by collar 22, with collar 22 surrounding a distal portion of fastener guide 20. The user can place distal ends 46, 48 in hole 18 and threadably engages the threads of distal ends 46, 48 with the threads of hole 18 of bone plate 16. After threadably engaging distal ends 46, 48 with the threads of hole 18, fastener 14 is inserted by the user into through-bore 44 at the proximal end of fastener guide 20 (it can be appreciated that this insertion of fastener 14 in through-bore 44 can occur before distal ends 46, 48 engage with hole 18, so long as distal ends 46, 48 are in the closed position). Beams 49 may hold fastener 14 within through-bore 44. Then, the user can position drill 12 above fastener 14, with elongated driver 30 extending towards the head of fastener 14, drill 12 being used to advance fastener 14 into bone through hole 18 of bone plate 16. Elongated driver 30 can descend towards fastener 14 so as to engage the head of fastener 14. As elongated driver 30 turns fastener 14 clockwise (viewed from the top looking down on fastener 14), fastener 14 descends down through through-bore 44. As the head of fastener 14 reaches distal ends 46, 48, fastener 14 would be blocked from descending any further, so long as fastener guide 20 is in the closed position. However, as fastener 14 descends, collar 22 engages with fastener guide 20, as indicated in FIG. 10. When collar 22 engages with fastener guide 20, collar 22 begins to turn fastener guide in the counter-clockwise direction, by way of the aforementioned gearing, and thus opposite the direction of fastener 14. Thus, as elongated driver 30 drives fastener 14 and turns fastener 14 in the clockwise direction, collar 22 turns fastener guide 20 counter-clockwise, so as to unthread fastener 14 from bone plate 18. That is, this turning of fastener guide 20, by a reversing driver, in the opposite direction of fastener 14 causes fastener guide 20 to unthread from hole 18. More specifically, prior to fastener 14 completely seating in hole 18, protrusions inside collar 22 can engage the slots in which beams 49 are positioned, or any other suitable slots (which can be formed in the proximal end of sections 40, 42 and be open at the proximal edge of sections 40, 42). In so engaging such slots, collar can rotate fastener guide member 20 in the counterclockwise direction and out of the hole 18 (FIG. 10). When distal ends 46, 48 disengage (i.e., unthreads) from hole 18, leaf springs 41, 43, because of their bias, pop out radially outwardly, causing distal ends 46, 48 of sections 40, 42 to spread apart from one another, and in so doing space is made for the head of fastener 14 to continue to descend, down and away from fastener guide 20, so that the head of fastener 14 can seat in hole 18 of bone plate 16. Though not shown, threads on shaft of fastener 14 engage with bone, so as to fix bone plate 16 to bone. Thereby, fastener alignment is advantageously maintained, because fastener 14 is substantially inserted into the bone before fastener guide 20 is removed from bone plate 16. Additionally, the user may insert multiple fastener guide members 20 into respective holes 18 in the bone plate 16, thus pre-aligning numerous fasteners 14 which are ready to be inserted into the bone via driven guide 10.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:
1. A fastener guide system, comprising:
a fastener; and
a fastener guide, comprising:
    a first longitudinal body portion including a first distal segment;
    a second longitudinal body portion including a second distal segment, the first longitudinal body portion connected to the second longitudinal body portion to form a fastener through-bore therebetween into which the fastener can be received for guiding the fastener into a hole in a bone plate, wherein the first longitudinal body portion being connected to the second longitudinal body portion comprises a flexible connection between the first longitudinal body portion and the second longitudinal body portion that allows the fastener guide to move between an open position and a closed position, wherein, in the closed position, a spacing of the first distal segment and the second distal segment relative to one another is such that a combination of the first distal segment and the second distal segment can be received in the hole in the bone plate for attaching the fastener guide to the bone plate, and wherein, in the open position of the fastener guide, said combination can no longer be received in the hole in the bone plate due to the first distal segment and the second distal segment being spaced relatively further apart from one another in comparison to the spacing in the closed position of the fastener guide;
    a first retaining member incorporated into the first longitudinal body portion for retaining the fastener in the fastener through-bore, wherein at least part of the first retaining member is positioned proximally of the connection along the fastener guide; and
    a first biasing element incorporated into the first longitudinal body portion and a second biasing element incorporated into the second longitudinal body portion for biasing the fastener guide toward the open position when in the closed position, said biasing able to occur independently of receiving the fastener in the fastener through-bore, wherein at least part of the first biasing element is positioned distally of the connection along the fastener guide, and wherein at least part of the second biasing element is positioned distally of the connection along the fastener guide,
wherein the first biasing element and the second biasing element are formed unconnected to one another, the first biasing element comprising a first proximal end connected to the first longitudinal body portion and a first free distal end adjacent the first distal segment, the second biasing element comprising a second proximal end connected to the second longitudinal body portion and a second free distal end adjacent the second distal segment, and wherein, in the closed position of the fastener guide, the first free distal end of the first biasing element and the second free distal end of the second biasing element are in opposing contact with one another and thereafter can exert force against one another to move the fastener guide from the closed position to the open position.
2. The fastener guide system of claim 1 in combination with a bone plate, wherein the fastener is received and retained in the fastener through-bore with the fastener guide attached to the bone plate in the closed position.

3. The fastener guide system of claim 1, wherein each of the first distal segment and the second distal segment incorporates a threaded section.

4. The fastener guide system of claim 1, wherein the first biasing element is machined into the first longitudinal body portion, and wherein the second biasing element is machined into the second longitudinal body portion.

5. The fastener guide system of claim 1, wherein the first longitudinal body portion incorporates a first pair of biasing elements which includes the first biasing element, and the second longitudinal body portion incorporates a second pair of biasing elements which includes the second biasing element.

6. The fastener guide system of claim 5, wherein the first pair of biasing elements comprises a first pair of spring elements machined into the first longitudinal body portion, and wherein the second pair of biasing elements comprises a second pair of spring elements machined into the second longitudinal body portion.

7. A fastener guide, comprising:
a first longitudinal body portion including a first threaded distal segment;
a second longitudinal body portion including a second threaded distal segment, the first longitudinal body portion connected to the second longitudinal body portion to form a fastener through-bore therebetween into which a fastener can be received for guiding the fastener into a hole in a bone plate, wherein the first longitudinal body portion being connected to the second longitudinal body portion comprises a pivot connection between the first longitudinal body portion and the second longitudinal body portion to allow the fastener guide to move between an open position and a closed position, wherein, in the closed position, a spacing of the first threaded distal segment and the second threaded distal segment relative to one another is such that a combination of the first threaded distal segment and the second threaded distal segment can be threadably received in the hole in the bone plate for attaching the fastener guide to the bone plate, and wherein, in the open position of the fastener guide, said combination can no longer be threadably received in the hole in the bone plate due to the first threaded distal segment and the second threaded distal segment being spaced relatively further apart from one another in comparison to the spacing in the closed position of the fastener guide;
a first retaining member incorporated into the fastener guide for retaining the fastener in the fastener through-bore; and
a first spring element machined into the first longitudinal body portion and a second spring element machined into the second longitudinal body portion for biasing the fastener guide toward the open position when in the closed position, wherein at least part of the first spring element is positioned distally of the pivot connection along the fastener guide, and wherein at least part of the second spring element is positioned distally of the pivot connection along the fastener guide, the first spring element comprising a first proximal end connected to the first longitudinal body portion and a first free distal end adjacent the first threaded distal segment, the second spring element comprising a second proximal end connected to the second longitudinal body portion and a second free distal end adjacent the second threaded distal segment, wherein the first spring element and the second spring element are formed unconnected to one another, and wherein, in the closed position of the fastener guide, the first free distal end of the first spring element and the second free distal end of the second spring element are in opposing contact with one another and thereafter can exert force against one another to move the fastener guide from the closed position to the open position.

8. The fastener guide of claim 7, wherein at least part of the first retaining member is positioned proximally of the pivot connection along the fastener guide.

9. The fastener guide of claim 8, wherein the entirety of the first retaining member is positioned proximally of the pivot connection along the fastener guide.

10. The fastener guide of claim 7, wherein the first retaining member is incorporated into the first longitudinal body portion.

11. The fastener guide of claim 7, wherein the entirety of the first spring element is positioned distally of the pivot connection along the fastener guide.

12. The fastener guide of claim 7 in combination with a bone plate, wherein the fastener guide is attached to the bone plate in the closed position.

13. A driven fastener guide for guiding a fastener into a hole of a bone plate, the driven fastener guide comprising:
an elongated driver configured for connecting to a drill;
a fastener guide member operably connected to the elongated driver, the fastener guide member including a first section and a second section which is pivotably connected to the first section, the first section and the second section defining a through-bore configured for receiving the fastener, the fastener guide member being configured for aligning the fastener relative to the hole of the bone plate, the first section including a first distal end, the second section including a second distal end, the first distal end and the second distal end being biased to an open position relative to one another, the first section including a first pair of spring elements, the second section including a second pair of spring elements, wherein each spring element of the first pair of spring elements comprises a first proximal end connected to the first section and a first free distal end adjacent the first distal end of the first section, and wherein each spring element of the second pair of spring elements comprises a second proximal end connected to the second section and a second free distal end adjacent the second distal end of the second section, wherein the first pair of spring elements is formed unconnected to the second pair of spring elements, and wherein the first free distal ends of the first pair of spring elements and the second free distal ends of the second pair of spring elements are in opposing contact with one another to exert force against one another for biasing the first distal end of the first section and the second distal end of the second section to the open position.

14. The driven fastener guide of claim 13 in combination with a fastener receivable in the through-bore.

15. The driven fastener guide of claim 13, wherein the fastener guide member includes a belt which pivotably connects the first section and the second section together.

* * * * *

UNITED STATES PATENT AND TRADEMARK OFFICE
CERTIFICATE OF CORRECTION

PATENT NO. : 12,426,900 B2  
APPLICATION NO. : 18/108908  
DATED : September 30, 2025  
INVENTOR(S) : Jason F. Detweiler Page 1 of 1

It is certified that error appears in the above-identified patent and that said Letters Patent is hereby corrected as shown below:

In the Claims

In Column 10, Lines 18-19, in Claim 1, after "a", delete "flexible"

Signed and Sealed this
Thirtieth Day of December, 2025

John A. Squires
*Director of the United States Patent and Trademark Office*